United States Patent [19]
Hanauye et al.

[11] 3,933,928
[45] Jan. 20, 1976

[54] METHOD FOR PRODUCING 2,6-DI-TERT.-BUTYL-4-CUMYL PHENOL

[75] Inventors: Kunio Hanauye; Tsutomu Takase, both of Nagoya; Mitsuhiro Iwasa, Tokai; Mizuo Ito, Nagoya, all of Japan

[73] Assignee: Mitsui Toatsu Chemicals, Incorporated, Tokyo, Japan

[22] Filed: Aug. 21, 1974

[21] Appl. No.: 499,546

[30] Foreign Application Priority Data
Aug. 27, 1973 Japan.................................. 48-95139

[52] U.S. Cl....... 260/626 R; 260/624 R; 260/624 C
[51] Int. Cl.².......................................... C07C 39/06
[58] Field of Search........ 260/624 R, 624 C, 626 R, 260/619 A, 626 T, 624 A, 624 E

[56] References Cited
UNITED STATES PATENTS

| | | | |
|---|---|---|---|
| 3,116,336 | 12/1963 | Van Winkle........................ | 260/624 |
| 3,177,259 | 4/1965 | Van Winkle........................ | 260/624 |
| 3,711,559 | 1/1973 | Ensvr................................ | 260/619 A |

Primary Examiner—James O. Thomas, Jr.
Assistant Examiner—W. B. Lone
Attorney, Agent, or Firm—Fisher, Christen & Sabol

[57] ABSTRACT

2,6-di-tert.-butyl-4-cumyl phenol is produced by reacting p-cumyl phenol with isobutylene, at a reaction temperature of from 40° to 120°C. in the presence of from 0.01 to 20% by weight of p-toluene sulfonic acid based on the weight of the p-cumyl phenol. Isobutylene is charged into the reaction system at a high rate and is always present in the reaction system during the reaction. A substantially 100% conversion of p-cumyl phenol is attained and the weight ratio of 2,6-di-tert.-butyl-4-cumyl phenol/2-tert.-butyl-4-cumyl phenol in the reaction product is greater than 10, while splitting off of the cumyl group at the para position is suppressed.

6 Claims, No Drawings

3,933,928

METHOD FOR PRODUCING 2,6-DI-TERT.-BUTYL-4-CUMYL PHENOL

BACKGROUND OF THE INVENTION

1. Field of the Invention

The present invention relates to a method for producing 2,6-di-tert.-butyl-4-cumyl phenol by reacting p-cumyl phenol with isobutylene. More particularly, the present invention relates to such a method wherein p-toluene sulfonic acid is used as a catalyst in the reaction.

2,6-di-tert.-butyl-4-cumyl phenol produced according to the present invention is a white crystalline compound useful as antioxidant for various plastic materials and as an insecticide having particular effectiveness upon mosquito larvae.

2. Description of the Prior Art

Many methods have hitherto been known for introducing the tert.-butyl radical into the nucleus of phenols. There are known, for example, a method in which phenols are reacted with tert.-butyl chloride using aluminum chloride or phosphoric acid-boron trifluoride as catalyst, and a method in which phenols are reacted with isobutylene using a catalyst such as sulfuric acid, aluminum chloride, boron trifluoride-phosphoric acid, a cation exchange resin, phosphoryl trichloride, zinc oxide or Japanese acid clayzinc chloride. However, most of these known reactions are effective for introducing the tert.-butyl radical into the para position to the hydroxyl group of the phenol and are inadequate for introducing two tert.-butyl radicals into the ortho positions. Applicants are unaware of any prior art disclosure regarding application of these reactions for ortho position di-tert.-butylation of p-cumyl phenol. This has also been verified in investigations made by applicants which show the above reactions to be unfavorable, since the splitting off of the cumyl group at the para position has, due to the high activities of the catalysts, proceeded considerably under reaction conditions otherwise favorable for the tert.-butylation to take place. In addition, while the splitting off of the cumyl group can be repressed when the reaction conditions are moderated, for example, by decreasing the amount of catalyst, it is only possible to introduce one tert.-butyl radical into the ortho position, so that such measures also fail to introduce two tert.-butyl radicals into the nucleus of the phenol.

In addition to the reactions described above, other reactions have been known for introducing alkyl groups selectively into the ortho positions of phenols. For example, there is proposed in U.S. Pat. No. 2,831,898, an ortho-alkylation of phenols with olefins using a phenoxide of aluminum or magnesium as catalyst and it is known from the examples of Japanese published patent application Sho-47-3322 to introduce a tert.-butyl radical into the ortho position of a phenol with tert.-butyl alcohol using tellurium dioxide as catalyst. However, since both of these references teach a method in which either a mixture of mono- and de-substitution of the ortho position or mono-substitution alone is produced, they are not suited for obtaining solely the ortho-di-substitution. Moreover, if the catalyst of U.S. Pat. No. 3,831,898 is used to achieve ortho-alkylation of p-cumyl phenol, then the catalyst should be in the form of aluminum-p-cumyl phenoxide, which has been found by research of applicants to have very low catalytic activity so that the di-substituted product has not been obtained in suitable yield.

Furthermore, it is proposed in Bull. Soc. Chem. Belg., 26, 308 (1912) as well as in U.S. Pat. No. 2,865,966, to use p-toluene sulfonic acid as a catalyst for the alkylation of phenols. However, in these reactions, the para position of the phenol is alkylated. Furthermore, it is disclosed in U.S. Pat. No. 3,082,258 to use a hydrated product of methane disulfonic acid or methane trisulfonic acid as catalyst in producing 2,6-di-tert.-butyl-4-methyl phenol by the alkylation of p-cresol with isobutylene. Here, it was also taught that when p-toluene sulfonic acid or sulfuric acid is used as catalyst in such a disubstitution reaction, a product of inferior quality such as with coloration and odor will be obtained. However, if methane disulfonic acid or methane trisulfonic acid is used as catalyst in the alkylation of p-cumyl phenol with isobutylene, even though the splitting off of the cumyl group at the para position is considerably suppressed, the formation of 2-tert.-butyl-4-cumyl phenol, which is especially difficult to separate from 2,6-di-tert.-butyl-4-cumyl phenol as will be described hereinafter, can not sufficiently be reduced, so that the after treatment of the reaction product becomes very difficult and purification methods are uneconomical. In addition, the yield of the reaction may be lowered unfavorably, since p-cumyl phenol remains unreacted or the etherified product of p-cumyl phenol, i.e. tert.-butyl ether, is formed, both in considerable amounts.

As described above, it is impossible to obtain the disubstituted product at a high yield by the methods taught by the prior art because a considerable amount of mono-substitution product is formed and, at the same time, the splitting off of the cumyl group at the para position occurs.

Moreover, according to research by applicants, when the mono-substituted product is contained in the reaction product, it can hardly be removed by usual purification procedure such as recrystallization or distillation. In this case, the selective salt formation of the mono-substituted product by an alkali such as sodium hydroxide is also found ineffective. When the mono-substituted product is contained in the final product in a substantial amount, difficulties may arise; for example, it will cause a marked coloration of the product with the passage of time, because the mono-substituted product will be more readily oxidized when compared to 2,6-di-tert.-butyl-4-cumyl phenol and, therefore, lowering of the mono-substituted product during the reaction is very important.

SUMMARY OF THE INVENTION

Applicants herein, under the background described above, have invented a method for producing 2,6-di-tert.-butyl-4-cumyl phenol economically and at high yield by the reaction of p-cumyl phenol with isobutylene in the presence of p-toluene sulfonic acid as a catalyst. The invention is further characterized in that the reaction is carried out at a reaction temperature of from 40° to 120°C. in the presence of p-toluene sulfonic acid in an amount of 0.01 to 20% by weight based upon the amount of p-cumyl phenol. By selecting the above reaction conditions and using p-toluene sulfonic acid as catalyst, a substantially 100% conversion of p-cumyl phenol can be attained and, at the same time, a weight ratio of [2,6-di-tert.-butyl-4-cumyl phenol]/[2-tert.-butyl-4-cumyl phenol] in the reaction product of more than 10 can be reached, while the splitting off of the cumyl group from the para position is represented to the utmost. Since the weight ratio of di-substituted product/mono-substituted product in the reaction product is greater than 10, a product having sufficient quality for practical use as an antioxidant for plastics as well as for an insecticide can be obtained by merely removing the catalyst from the reaction product and, in the case of a reaction in a solvent, by further removal of the solvent.

DESCRIPTION OF THE PREFERRED EMBODIMENT

The p-toluene sulfonic acid is used as catalyst in an amount of from 0.01 to 20% by weight based upon the amount of p-cumyl phenol, and an amount ranging from 0.1 to 5% weight is preferred. Use of the catalyst in an amount below 0.01% by weight will result in a very low reaction velocity and is not only impractical but it also becomes increasingly difficult to attain a weight ratio of di-substituted product/mono-substituted product of greater than 10. On the other hand, use of the catalyst in an amount above 20% by weight is also unfavorable because splitting off of the cumyl group at the para position will tend to occur and this will lower the yield of the reaction as well as of purified reaction product. While the reaction can be conducted without a solvent, it is also possible to use an inert organic solvent such as, for example, an aliphatic hydrocarbon, e.g., a-heptane, or an aromatic hydrocarbon, e.g., benzene or toluene. Since the melting point of p-cumyl phenol is 74°C., it is suitable to conduct the reaction without solvent at a temperature above 74°C. However, it is also possible to carry out the reaction at a lower temperature when a solvent is used. The reaction temperature may thus be from 40° to 120°C. and preferably from 50°C to 80°C. Below 40°C. the alkylation reaction becomes too slow to be practical and above 120°C. splitting off of the cumyl group at the para position will occur to a substantial degree even when the other reaction conditions are varied in any manner, sothat the yield of reaction as well as of refined product is markedly lowered.

The reaction can be carried out either at normal pressure or under elevated pressure, e.g., of from 0.2 to 3.5 kg/cm² gauge, and the supply of isobutylene may be charged by blasting it into the reaction liquid in a continuous or batchwise manner or by compressing it onto the surface of the reaction liquid. The amount of isobutylene to be charged should be greater, and preferably substantially greater, than that required stoichiometrically for the reaction, and it is essential that isobutylene is always present in the reaction system during the reaction.

Since the rate of reaction which takes place according the present invention is very rapid and accompanied by substantial heat evolution, it is necessary to either adopt a cooling operation, because of necessity of keeping the reaction temperature at below 120°C., or to control the rate of charging the isobutylene. However, the present inventors have found that the charging rate of isobutylene in the initial phase of the reaction should preferably be maintained as high as possible by the use of external cooling means, because the higher the rate of charging isobutylene at the initial stage of the reaction, the smaller the amount of the by-product concomitant to the splitting off of the cumyl group at the para position. The temperature of the reaction is maintained at 120°C. or below by the usual cooling means.

Using the reaction conditions described above, it has now become possible to convert substantially 100% of the p-cumyl phenol and, at the same time, to decrease the amount of mono-substituted product formed, which is particularly difficult to separate from 2,6-di-tert.-butyl-4-cumyl phenol, to an extent of 1 part by weight or below per 10 parts by weight of the di-substituted product.

To refine the reaction mixture, it is first necessary to remove the catalyst, and neutralization with an alkali or a water wash is preferred. When the reaction is conducted without solvent, the reaction product may at times be a solid, and in such a case, it is possible to convert the reaction product into a solution by using a suitable solvent before it is subjected to water wash or neutralization.

According to the reaction of the present invention, it is possible to obtain 2,6-di-tert.-butyl-4-cumyl phenol of sufficient purity for practical use by removal of the catalyst only, as the amount of by-products is small. However, if a higher quality is desired, it is possible to remove substantially all the low boiling by-products such as oligomers of isobutylene, dimers of α-methyl styrene and di- and tri-tert.-butylated compounds of the phenol as well as the higher boiling by-products, such as 2,4-di-cumyl phenol, 2,4-di-cumyl-6-tert.-butyl phenol, etc. by distillation or recrystallization after the catalyst is removed.

As seen from the foregoing, according to the method of the present invention, a tert.-butyl radical can be introduced into each of the two ortho positions of p-cumyl phenol with simultaneous suppression of splitting off of the para position cumyl group and this cannot be attained by any prior art method of di-tert.-butylation of the ortho position of p-cumyl phenol. Furthermore, the method according to the present invention is most efficient and economical for producing 2,6-di-tert.-butyl-4-cumyl phenol. This will be more fully understood from the examples and comparison examples which follow. In all of the examples, the stated reaction temperatures were maintained with external cooling wherever necessary.

EXAMPLE 1

100 grs. of p-cumyl phenol and 1 gr. of p-toluene sulfonic acid were placed in a 200 ml flask having four mouths and isobutylene was charged thereinto at the rate of 200 ml/min. at 80°C. under agitation. All of the p-cumyl phenol had been reacted after 2 hours. After the agitation was further continued for 1 hour, the reaction mixture was colorless and transparent, and the composition thereof was 92.2% of 2,6-di-tert.-butyl-4-cumyl phenol (hereinafter called di-substituted product), 5.4% of 2-tert.-butyl-4-cumyl phenol (hereinafter called mono-substituted product) and 2% of other by-products. Total amount of isobutylene charged was 56.7 grs (7.8% excess). The p-toluene sulfonic acid in the reaction mixture was neutralized by adding an excess equivalence of a 50% solution of sodium hydroxide and then distillation was carried out under a reduced pressure of 1 mm Hg. 137 grs. of a distillation fraction of 145°–148°C. b.p./1mm Hg were obtained (total yield 89.5%). This converted into a white crystalline mass on cooling and the content of the di-substituted product was 98.8%.

EXAMPLE 2

A reaction mixture obtained in the same manner as in Example 1 was poured into a dilute aqueous solution of sodium hydroxide and agitated vigorously to neutralize the p-toluene sulfonic acid. The reaction product was converted into a finely dispersed slurry, which was then filtered, water washed and dried under reduced pressure. 141 grs. of slightly yellowish crystals were obtained (total yield 92.9%). The content of di-substituted product was 95.1%.

EXAMPLE 3

100 grs. of p-cumyl phenol, 100 grs. of benzene and 5 grs. of p-toluene sulfonic acid were placed in a 300 ml flask having four mouths and isobutylene was charged at a rate of 200 ml/min. at 50°–60°C. under agitation. The composition of the reaction mixture after 4.5 hours was 56.6% of di-substituted product, 1.3% of mono-substituted product and 2% of other by-products with the remainder benzene. Total amount of isobutylene charged was 62 grs (17% excess). This reaction mixture was neutralized with a 10% aqueous solution of sodium hydroxide in equal equivalence with the p-toluene sulfonic acid and, after a water wash, distillation was carried out under vacuum with addition of a fiarly small amount of solid sodium hydroxide. 136 grs. of a fraction of 146°–148°C. b.p./1mm Hg were obtained (total yield 89.0%). The di-subsituted product obtained had a purity of more than 99.5% and it was a white crystalline mass having a melting point of 73°C.

EXAMPLE 4

A reaction mixture obtained by the same method as in Example 3 was neutralized and water washed, also in the same manner, and then benzene and water were removed therefrom under vacuum. The low boiling by-products were removed at the same time and there were obtained 145 grs. of slightly yellowish crystals after cooling (total yield 94.8%). The content of di-substituted product was 95.4%.

EXAMPLE 5

100 grs. of p-cumyl phenol, 100 grs. of benzene and 5 grs. of p-toluene sulfonic acid were placed in a 300 ml autoclave made of glass and isobutylene was charged thereinto at 40°–55°C. with agitation and maintained under a pressure of 0.5–1.7 kg/cm² gauge. The composition of the reaction mixture after 6 hours was 56.3% of di-substituted product, 2.1% of mono-substituted product and 1% of other by-products with the remainder benzene. Total amount of isobutylene charged was 68 grs (30% excess). Neutralization of p-toluene sulfonic acid was conducted as in Example 3 and, after distillation, 136 grs. of a fraction of 145°–148°C. b.p./1mm Hg were obtained (total yield 89.0%). The content of di-substituted product was 99.0%.

EXAMPLE 6

10 grs. of p-cumyl phenol and 0.5 gr. of p-toluene sulfonic acid were placed in a 50 ml flask having four mouths and isobutylene was charged thereinto at a rate of 53 ml/min. at 80°C. under agitation. All the p-cumyl phenol was reacted within 30 minutes and the agitation was further maintained for 1 additional hours. The ratio of formation of the main products in the reaction mixture, i.e. the ratio of di-substituted product/mono-substituted product (hereinafter referred to as production ratio), was found to be 15 and about 5% of a by-product concomitant to the splitting off of the para position cumyl group was recognized.

EXAMPLE 7

The reaction was carried out as in Example 6 with the exception that the amount of p-toluene sulfonic acid was 0.05 gr. Most of the p-cumyl phenol was reacted within 2 hours and the production ratio of the main products after agitation was further continued for 2 hours was 11. After standing one night at room temperature, the production ratio of the reaction mixture was raised to 15. No by-product concomitant to splitting off of the para position cumyl group was recognized.

EXAMPLE 8

The reaction was carried out as in Example 6, with the exception that the amount of p-toluene sulfonic acid was changed to 0.1 gr. and the temperature was 100°C. All the p-cumyl phenol had reacted within 1.5 hours and the production ratio of main products after further agitation for 2 hours was 10. About 3% of by-product concomitant to splitting off of the para position group was recognized.

Comparison Example 1

10 grs. of p-cumyl phenol, 10 grs. of benzene and 0.5 gr. of methane disulfonic acid di-hydrate as catalyst in place of p-toluene sulfonic acid were placed in a 50 ml flask with four mouths and isobutylene was introduced at the rate of 53 ml/min. under agitation at 40°C., which is equal to the reaction temperature given examples of U.S. Pat. No. 3,082,258. The reaction rate was slow compared to that when using p-toluene sulfonic acid and it was necessary to slow down the rate of introduction of isobutylene due to an incresase of recovery of unreacted isobutylene. The composition of the reaction mixture became nearly constant after 5 hours and, after further agitation for 2 hours, was 37.7% of di-substituted product, 7.3% of mono-substituted product (the production ratio was therefore 5.2) and 4.6% of unreacted p-cumyl phenol and tert.-butyl ether of p-cumyl phenol with the remainder benzene. Some by-products concomitant to the splitting off of the cumyl group at the para position were recognized.

Comparison Example 2

The reaction in Comparison Example 1 was repeated at a reaction temperature of 60°C. However, the reaction rate was still slow and the reaction temperature was raised to 70°C. after 2 hours and was further raised to 80°C. after 1 hour. The composition of the reaction mixture became nearly constant after the agitation was continued for 0.5 hour at 80°C. After the agitation was further continued for 1 hour, the composition of the reaction mixture was found to be 49.3% of di-substituted product, 6.1% of mono-substituted product (the production ratio was therefore 8.1) and 1.6% of unreacted p-cumyl phenol and tert.-butyl ether of p-cumyl phenol with the remainder benzene. The by-product concomitant to the splitting off of the para position cumyl group was in a greater amount than in Comparison Example 1.

Comparison Example 3

The reaction of Comparison Example 1 was repeated with the exception that 1.0 gr. of methane disulfonic acid dihydrate was used as catalyst and the reaction temperature was maintained at 70°–80°C. The reaction rate was slow as in Comparison Example 1 and the composition of the reaction mixture became substantially constant after 6 hours. After the agitation was continued for 7.5 hours, the composition of the reaction mixture was found to be 41.4% of di-substituted product, 8.6% of mono-substituted product (the production ratio was therefore 4.8) and 3.3% of unreacted p-cumyl phenol and tert.-butyl ether of p-cumyl phenol with the remainder benzene. The amount of by-product concomitant to the splitting off of the para position cumyl group was greater than in Comparison Example 1.

What is claimed is:

1. A method for producing 2,6-di-tert.-butyl-4-cumyl phenol by reacting p-cumyl phenol with isobutylene which comprises conducting the reaction in the presence of p-toluene sulfonic acid in an amount of from 0.01 to 20% by weight based upon the amount of p-cumyl phenol and at a reaction temperature of from 40° to 120°C.

2. The method according to claim 1 wherein the p-toluene sulfonic acid is present in an amount of from 0.1 to 5% by weight based upon the amount of p-cumyl phenol.

3. The method according to claim 1 wherein the reaction temperature is from 50° to 80°C.

4. The method according to claim 1 wherein the p-toluene sulfonic acid is present in an amount of from 0.1 to 5% by weight based upon the amount of p-cumyl phenol and the reaction temperature is between 50° and 80°C.

5. The method according to claim 1 wherein, after said reaction, the p-toluene sulfonic acid is neutralized by adding an excess equivalence of alkali to the reaction mixture and thereafter subjecting the reaction mixture to a distillation under reduced pressure.

6. The method according to claim 1 wherein the isobutylene is charged into the reaction system in an amount in excess of that stoichiometrically required and at a rate wherebby isobutylene is always present in the reaction system for the duration of the reaction.

* * * * *

UNITED STATES PATENT OFFICE
CERTIFICATE OF CORRECTION

PATENT NO. : 3,933,928
DATED : January 20, 1976
INVENTOR(S) : Kunio HANAUYE et al.

It is certified that error appears in the above-identified patent and that said Letters Patent are hereby corrected as shown below:

Col. 1, line 61 "de-" should be --di- --

Col. 3, line 3 "represented" should be --repressed--

Col. 3, line 30 "a-heptane" should be --n-heptane--

Col. 6, line 30 "given exam-" should be --given in exam- --

Claim 6, line 4 "wherebby" should be --whereby--

Signed and Sealed this

Twenty-eighth Day of June 1977

[SEAL]

Attest:

RUTH C. MASON
*Attesting Officer*

C. MARSHALL DANN
*Commissioner of Patents and Trademarks*